(12) United States Patent
Nielsen et al.

(10) Patent No.: US 6,332,879 B1
(45) Date of Patent: Dec. 25, 2001

(54) OSTOMY APPLIANCE

(75) Inventors: Inger Mann Nielsen, Frederiksberg; Eskil Hoejland Olsen, Klampenborg; Laila Busk Gothjaelpsen, Hvidovre; Carsten Sletten, Koebenhavn; Danuta Ciok, Nivaa, all of (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 09/424,230

(22) PCT Filed: May 25, 1998

(86) PCT No.: PCT/DK98/00212

§ 371 Date: Feb. 25, 2000

§ 102(e) Date: Feb. 25, 2000

(87) PCT Pub. No.: WO98/53771

PCT Pub. Date: Dec. 3, 1998

(30) Foreign Application Priority Data

May 26, 1997 (DK) .................................................... 0598/97
Dec. 22, 1997 (DK) .................................................... 1507/97

(51) Int. Cl.[7] ........................................................ A61F 5/44
(52) U.S. Cl. ........................... 604/344; 604/332; 604/336; 604/342
(58) Field of Search .................................. 604/322, 327, 604/332–345

(56) References Cited

U.S. PATENT DOCUMENTS

| 3,419,006 | 12/1968 | King . |
| 3,876,771 | 4/1975 | Denner .................................. 424/78 |
| 3,972,328 | 8/1976 | Chen . |
| 4,095,599 | 6/1978 | Simonet-Haibe . |
| 4,204,504 | 5/1980 | Cilento et al. . |

(List continued on next page.)

FOREIGN PATENT DOCUMENTS

| 147226 | 1/1977 | (DK) . |
| 0 048 556 | 3/1982 | (EP) . |
| 0 302 536 | 2/1989 | (EP) . |
| 0 415 183 | 3/1991 | (EP) . |
| 0 272 149 | 3/1992 | (EP) . |

(List continued on next page.)

OTHER PUBLICATIONS

Hellman, J. et al, "Dermatologic Complications in Colostomy and Ileostomy Patients", International Journal of Dermatology, vol. 29, No. 2, Mar. 1990, pp. 129–133.

Pearl, R. et al "Early Local Complications From Intestinal Stomas", Arch Surg, vol. 120, Oct. 1985, pp. 1145–1147.

*Primary Examiner*—Kim M. Lewis
(74) *Attorney, Agent, or Firm*—Jacobson Holman, PLLC

(57) ABSTRACT

The invention relates to an ostomy appliance comprising a body side member comprising an adhesive wafer or pad for securing the appliance to the user's skin, said wafer or pad having a hole for receiving a stoma, and an optionally separately exchangeable receiving member or bag secured to the body side ostomy member for receiving secretions from the ostomy, said ostomy appliance further comprising a sealing member disposed in the hole of the wafer or pad surrounding the stoma wherein the sealing member disposed in the hole of the wafer or pad surrounding the stoma, said sealing member having a hole for accommodating the stoma and said sealing member having balanced plastic and elastic properties allowing an adaptation of the hole of the ostomy appliance to a stoma by a temporary enlarging the hole by everting or rolling up the inner rim of the hole for accommodating the stoma. When the ostomy appliance of the invention has been placed over and around the stoma the adhesive sealing member may recover essentially to the original form to fit snugly to the stoma. Preferably at least the area of a release liner covering the separate sealing member is provided with a guide for adaptation of the hole of an ostomy appliance to the size of an ostomy, said guide being visible from the side of the release liner facing the sealing member.

10 Claims, 4 Drawing Sheets

U.S. PATENT DOCUMENTS

| | | |
|---|---|---|
| 4,367,732 | 1/1983 | Poulsen et al. . |
| 4,538,603 | 9/1985 | Pawelchak et al. . |
| 4,551,490 | 11/1985 | Doyle et al. .......................... 524/22 |
| 4,552,138 | 11/1985 | Hofeditz et al. . |
| 4,681,574 | 7/1987 | Eastman ............................. 604/344 |
| 4,750,482 | 6/1988 | Sieverding . |
| 4,867,748 | 9/1989 | Samuelsen ......................... 604/336 |
| 5,051,259 | 9/1991 | Olsen et al. ........................ 424/443 |
| 5,714,225 | 2/1998 | Hansen et al. ...................... 428/114 |

FOREIGN PATENT DOCUMENTS

| | | |
|---|---|---|
| 0 686 381 | 12/1995 | (EP) . |
| 1 208 631 | 7/1972 | (GB) . |
| 1 586 182 | 3/1981 | (GB) . |
| 2 290 974 | 1/1996 | (GB) . |
| WO88/06894 | 9/1988 | (WO) . |
| WO98/17212 | 4/1998 | (WO) . |

OSTOMY APPLIANCE

BACKGROUND OF THE INVENTION

The present invention relates to an ostomy appliance, an ostomy appliance body side member, an ostomy sealing member and to a method of applying an ostomy appliance body side member around a stoma.

DESCRIPTION OF THE RELATED ART

In connection with surgery for a number of diseases in the gastrointestinal tract a consequence is, in many cases, that the colon, the ileum or the urethra has been exposed surgically and the patient is left with an abdominal stoma and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma. Also in connection with a fistula, the patient will have to rely on an appliance to collect the bodily material emerging from such opening.

Ostomy appliances are well known. Such appliances may be two-piece or one-piece appliances. In both types of appliances, a body side member is attached to the wearer's abdomen, and optionally a receiving member or bag is attached to the body side ostomy member for receiving exudates from the ostomy in case of a two-piece appliance.

When using one-piece appliances, the whole appliance, including the adhesive wafer or pad securing the appliance to the skin, is removed and replaced by a fresh appliance. When using two-piece appliances, the body side ostomy member is let in place for several days, and only the receiving member or bag is replaced.

The service time of the body side ostomy member depends on the amount and aggressiveness of the exudates and of the tightness between the ostomy and the body side ostomy member.

In the known appliances it is necessary to change the body side member of a two-piece appliance when the center part of the adhesive wafer or pad had been sufficiently deteriorated to allow access of the aggressive exudates to the skin surrounding the stoma, irrespective of the fact that the wafer as such has a much longer wearing time. The access of aggressive exudates to the skin will cause skin problems.

Skin problems are common for persons having a stoma. Generally, about 40% have skin problems (Pearl et al. 1985 "Early local complications from intestinal stomas", Arch. Surg. 120; 1145–1147) and the frequency is especially high for persons having a urostomy or ileostomy. About 80% of the persons having an ileostomy have skin problems (Hellman, J. D., Lago, C. P. 1990 "Dermatologic complications in colostomy and ileostomy patients", International Journal of Dermatology, 29 (2); 129–133). The skin problems are more pronounced in a circular area about the stoma (½ inch from the stoma) (Hellman and Lago 1990).

Frequent changing of the body side member of a two-piece appliance or the frequent exchange of a one-piece appliance is undesirable due to the irritation of the skin and the quality of life may be improved and the nuisance of the wearing of an ostomy appliance reduced if the intervals between exchanging of the body side member can be increased.

It is known to place a ring on the skin before applying the body side member or to make a filling between the edge of the stoma and the shaped whole of the ostomy appliance in order to form a seal between the stoma and the ostomy appliance in order to alleviate the problems of using a commercially available medical grade adhesive paste. Such pastes are, e.g., sold by Bristol-Myers Squibb under the trademark Stomahesive® or by Coloplast under the trademark Coloplast® Paste.

These pastes, however, do not have a composition which has a sufficient cohesion to ensure safe removal thereof without leaving residues on the skin and, on the other hand, the pastes often are so sticky that they cannot easily be shaped using the finger without sticking to the finger. If using a paste, it should have a composition which is sufficiently tacky to secure the appliance or skin barrier to the abdomen and a cohesion ensuring safe removal thereof without leaving residues on the skin. On the other hand, the paste must not be so sticky that it cannot easily be shaped by a finger or hand without sticking to the hand. Furthermore, the paste must have a sufficient elasticity in order to be able to follow the movements of the patient without slipping on the skin and should also have a great resistance to erosion caused by aggressive exudates from an ostomy.

In GB Patent Application No. GB 2 290 974 is disclosed an ostomy appliance wherein a body-side member is combined with a moldable mass of non-hypoallergenic, non-memory putty-like adhesive, particularly based on a hydrocolloid or hydrogel. Thus, GB Patent Application No. GB 2 290 974 discloses a body-side ostomy member comprising a ring to which a bag-side coupling ring or a bag can be attached, the ring comprising a rib and a flange, the flange being mounted on a wafer of medical grade adhesive having a central whole of diameter of at least 65% of the internal diameter of the ring. A moldable mass of non-hypoallergenic, non-memory putty-like adhesive, particularly based on a hydrocolloid or hydrogel, is disposed radially inward of the wafer so that it forms a protective mass surrounding the stoma. The moldable mass has a thickness of 1.25–3 times that of the wafer and a central hole therein of a diameter no more than ⅒ of the internal diameter of the ring. Both the medical grade adhesive and the moldable adhesive are adhered to the skin.

The moldable mass of non-hypoallergenic, non-memory putty-like adhesive or flexible patch disclosed in GB Patent Application No. GB 2 290 974 is secured to the rim of the hole for receiving the stoma and may be displaced to engage with the stoma. The ostomy appliance disclosed in GB Patent Application No. GB 2 290 974 suffers from the drawback that the moldable sealing material is only foreseen to be changed together with the body side member of the appliance.

Furthermore, there is only disclosed that moldable sealing material is to be disposed or extruded towards the stoma which still leaves a considerable risk of an insufficient sealing as a sufficient amount of sealing material must be disposed to form a cohesive layer of adhesive sealing against the stoma. Thus, there is still a need for a sealing against a stoma which ensures that no leaks occur at the rim of the stoma and at the same time avoids the risk of thin spots or holes in the adhesive layer next to the stoma which may give rise to lack of protection of the skin next to the stoma and lead to a shorter service time between exchange of the body side member.

U.S. Pat. No. 4,095,599 discloses an ostomy appliance comprising a body side member comprising an adhesive wafer or pad for securing the appliance to the user's skin, said wafer or pad having a hole for receiving a stoma, and an optionally separately exchangeable receiving member or bag secured to the body side ostomy member for receiving secretions from the ostomy.

It has surprisingly been found that it is possible to provide an ostomy appliance having a separate or integrated sealing member disposed in the hole of the wafer or pad surrounding the stoma offering a convenient and comfortable solution to the above problems and which at the same time enables a separation of the two functions, the sealing around an ostomy and the securing of a separately exchangeable receiving member or bag for receiving secretions from an ostomy to a body side ostomy member.

None of the above mentioned patents describe the use of a separate sealing member which may be exchanged or substituted separately.

This idea according to the invention differs from the above mentioned patents since the central ring (sealing member) in this case in some embodiments can be substituted without substituting the adhesive of a body side member which carries the bag and further more in that the adaptation of the ostomy appliance to the specific ostomy is rendered very simple and independent of the use of tools and in that the adaptation of the appliance to the actual stoma is carried out by temporarily enlarging the central hole thereof and not by inward displacement of an adhesive mass to cover areas not covered hitherto to provide a snug engagement with the stoma.

BRIEF SUMMARY OF THE INVENTION

The invention relates in its broadest aspect to an ostomy appliance comprising a body side member, an optionally separately exchangeable receiving member or bag secured to the body side ostomy member and further a separate or integrated sealing member, the appliance having a guide for adaptation of an ostomy appliance to the size of an ostomy.

Furthermore, the invention relates to a separate sealing member for placing in a hole of an ostomy appliance.

Still further, the invention relates to an ostomy appliance body side member having a guide for adaptation of an ostomy appliance to the size of an ostomy as well as to different methods of applying an ostomy appliance body side member around a stoma by which the hole for receiving the stoma is adapted to the size of the stoma.

BRIEF DESCRIPTION OF THE DRAWINGS

The invention is disclosed in more detail with reference to the drawings in which.

DESCRIPTION OF THE PREFERRED EMBODIMENTS

Figure 1:
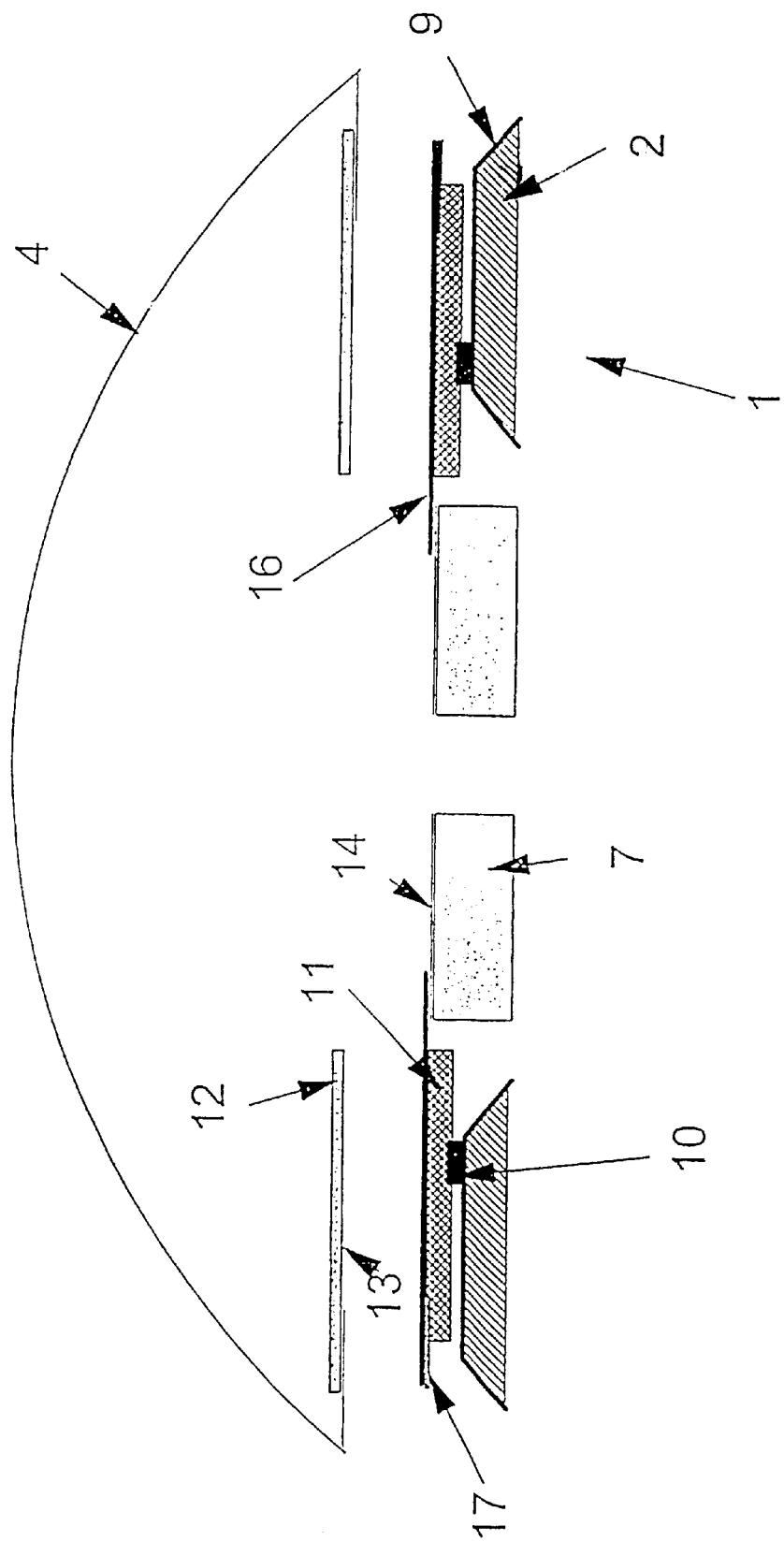
FIG. 1 shows a cross sectional view of an embodiment of an ostomy appliance of the invention.

Reference is made to FIG. 1 which shows an ostomy appliance according to the invention comprising a body side member 1 comprising an adhesive wafer or pad 2 for securing the appliance to the user's skin, the adhesive being covered by a film 9 conventionally used, e.g., a LDPE film. Furthermore, the body side member is secured by a sealing member 10 to a flange 11, preferably made from a foam material. A receiving member or bag 4 comprises a flange 12 secured to the flange 11 sealingly by a layer of an adhesive 13. The flange 12 may be welded to the receiving member 4 either inside the member or on the outside. The flange 11 preferably stretches beyond the inner rim of the wafer or pad 2 in order to prevent a moldable adhesive mass 7 of a separate sealing member from adhering to the wafer or pad. Such adherence might prevent the separate exchange of the sealing member independently of the exchange of the body side member. The separate sealing member may comprise a sheet 16 for adhering to the flange of body side member and for adhering the exchangeable receiving member or bag 4. At the outer rim of the flange 11, the sheet 16 preferably stretches beyond the rim of the flange to provide a handle 17 for gripping for separate exchange of the sealing member. Such handle preferably stretches over the full periphery in order to avoid adherence of the adhesive 13 of a separately exchangeable receiving member or bag 4 to the body side member 1. The handle may, e.g., be a slit liner. The adhesive 13 may be any adhesive being detachable from the two flanges in order to allow for an exchange of only the receiving member or bag 4 leaving the body side member 1 and the separate sealing member on the abdomen of the ostomate. It is desirable that the attachment between the receiving member or bag and the separate sealing member is weaker than the attachment between the separate sealing member and the body side member 1. The adhesive 13 may be an acrylic adhesive or any conventional skin friendly adhesive. Furthermore, the separate sealing member comprises a moldable backing 14. The backing preferably has a tensile strength of 2–5 N/m² at an elongation of 300%.

The separate sealing member may be made from a moldable adhesive in the form of a paste of a skin-friendly adhesive being sufficiently tacky to secure the appliance or skin barrier to the abdomen and a cohesion ensuring safe removal thereof without leaving residues on the skin. The sealing member may be composed of one material or may optionally be composed of two or more layers, one of which being a moldable backing which may optionally be covered with a protecting layer or film.

All adhesive surfaces may be protected by release liners to be removed before application.

The separate sealing member may be a uniform moldable mass of a hypoallergenic, substantially non-memory adhesive or it may comprise further constituents such as a protecting film or a moldable mesh.

The separate sealing member may be substituted together with the receiving member 4, leaving the body side member 1 on the skin. It is contemplated that the sealing member may be substituted independently of the receiving member according to the need of the user.

Figure 2:
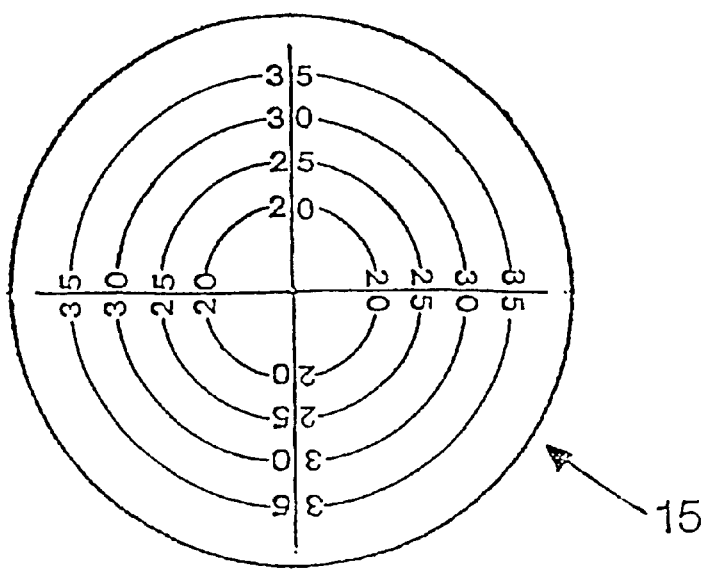
FIG. 2 shows a release liner having an indication of the size of the hole of an ostomy appliance of the invention for accommodating an ostomy.

Now referring to FIG. 2, a release liner 15 is shown having an indication of the size of the hole of an ostomy appliance of the invention for accommodating an ostomy at the side in contact with the separate sealing member (distal as compared to the ostomy). In the alternative, the indication may be placed on the side facing away from the separate sealing member (proximal as compared to the ostomy) if the release liner is transparent.

Figure 3:
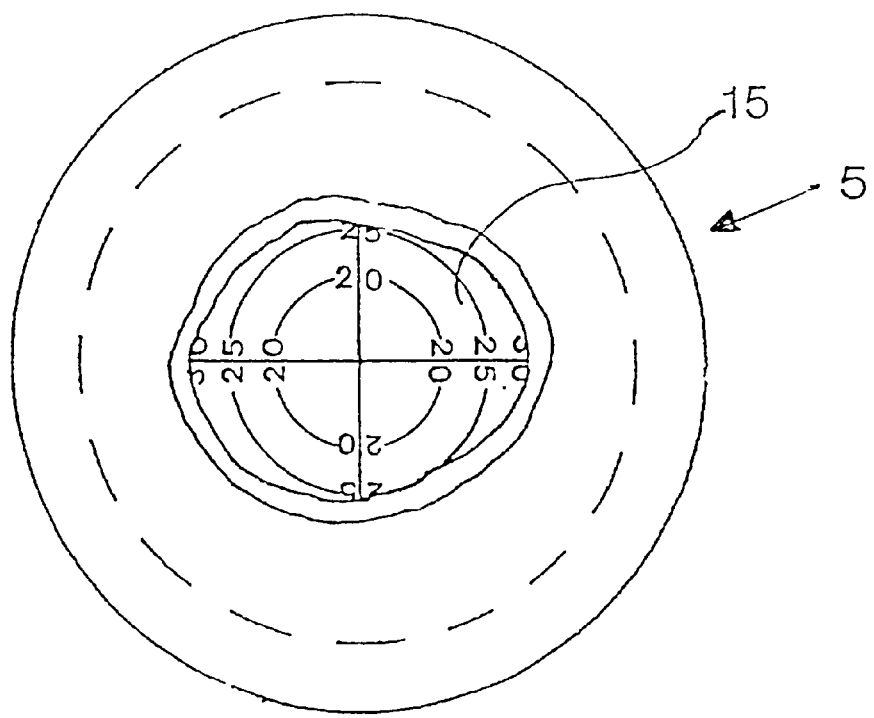
FIG. 3 shows a view from the distal side of the separate sealing member of an ostomy appliance of the invention in which the separate sealing member has been partially everted to increase the size of the hole of an ostomy appliance of the invention for accommodating an ostomy and showing the indication of the size of the hole placed on the release liner below.

FIG. 3 shows a view from the distal side of the separate sealing member 5 of an ostomy appliance of the invention in which the separate sealing member has been partially everted to increase the size of the hole of an ostomy appliance of the invention for accommodating an ostomy and showing the indication of the size of the hole placed on the release liner 15 below.

Figure 4:
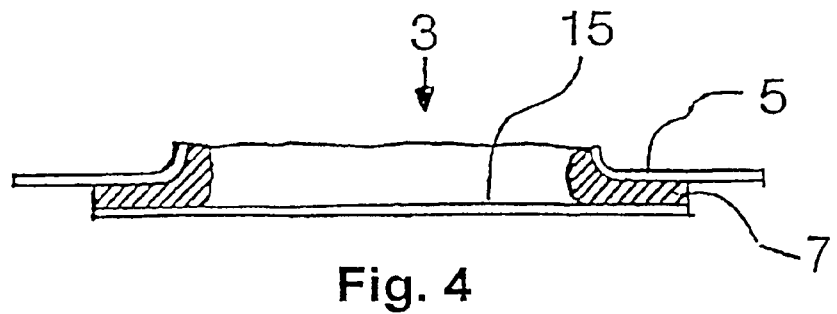
FIG. 4 shows a cross sectional view of the separate sealing member of FIG. 3.

FIG. 4 shows a cross sectional view of the separate sealing member of FIG. 3 wherein the sealing member 5 in the form of a uniform adhesive mass 7 has been partially everted enlarging the hole 3 and revealing a larger part of the surface of the release liner 15 below and of the indication of the size of the hole.

The adhesive and the adhesive wafer may be composed of a hypo-allergenic, soft, easily-deformable, non-memory putty-like adhesive material and is preferably a hydrocolloid based adhesive or a hydrogel. A moldable backing may, e.g., be a Parafilm® or made from a polymer solution which is sprayed on the surface and protects the surface of the adhesive against dissolution by secretions from the stoma and prevents a tacky surface on the side facing the bag. The moldable backing stretches out beyond the outer periphery of the ring in the form of a flange or adhesive layer. The moldable backing may have a tensile strength of from 1 to 10 N/mm$^2$, more preferred from 2 to 5 N/mm$^2$ and most preferred about 2.5 N/mm$^2$ at elongations up to 300%.

Figure 5:
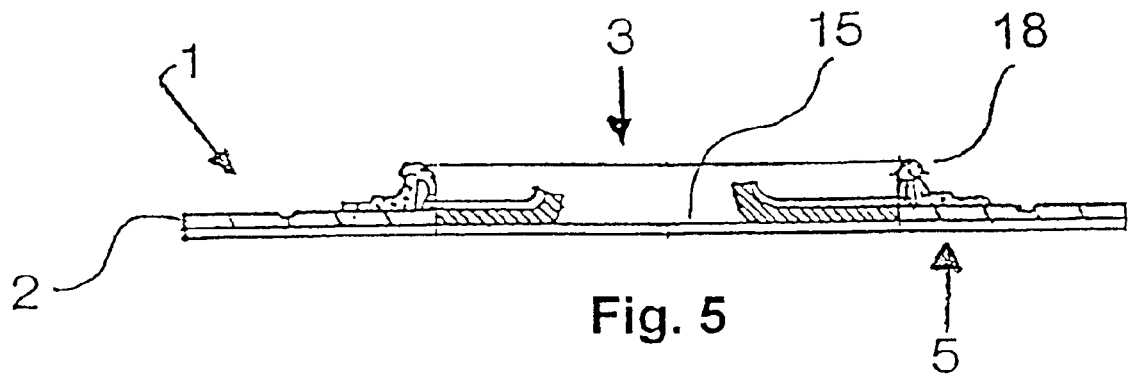
FIG. 5 shows a cross sectional view of an embodiment of an ostomy appliance body side member according to the invention.

FIG. 5 shows a cross sectional view of an embodiment of an ostomy appliance body side member 1 according to the invention comprising an adhesive wafer or pad 2 for securing the appliance to the user's skin; the adhesive may be covered by a film conventionally used. Furthermore, the body side member comprises a separate sealing member 5 disposed in the hole of the wafer or pad surrounding the stoma and a release liner 15. A receiving member or bag may be secured to a coupling ring 18.

Figure 6:
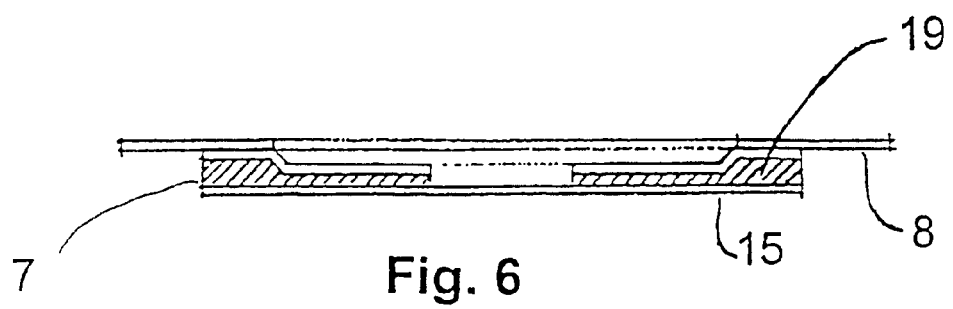
FIG. 6 shows a cross sectional view of a further embodiment of an ostomy appliance body side member according to the invention.

In the embodiment of FIG. 6 the sealing member is in the form of a uniform adhesive mass 7 which is thinner in the area next to the central hole for accommodating the stoma. The sealing member is provided with a flange 8 and a release liner 15 and a moldable backing 19. In an alternative embodiment of the invention, the adhesive wafer or pad of a body side member and the sealing member are integrated into one unit having the desired balanced plastic and elastic properties allowing an adaptation of the hole, the adhesive unit being thinner in the area next to the central hole for accommodating the stoma.

Figure 7:
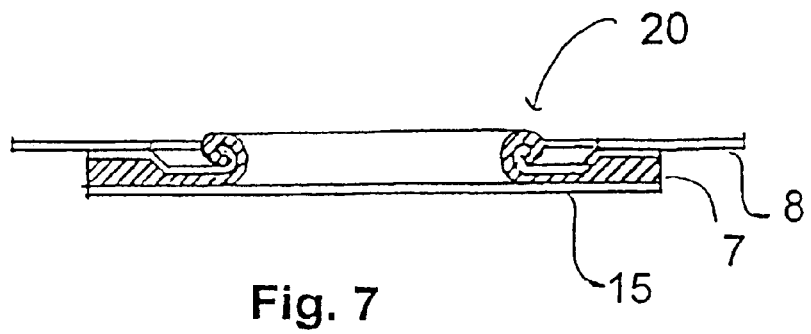
FIG. 7 shows a cross sectional view of the embodiment of FIG. 6 wherein the inner rim has been rolled up.

In FIG. 7, the rim of the central hole has been partially rolled up forming a torus 20 and revealing a larger part of the surface of the release liner 15 below and of the indication of the size of the hole.

Figure 8:
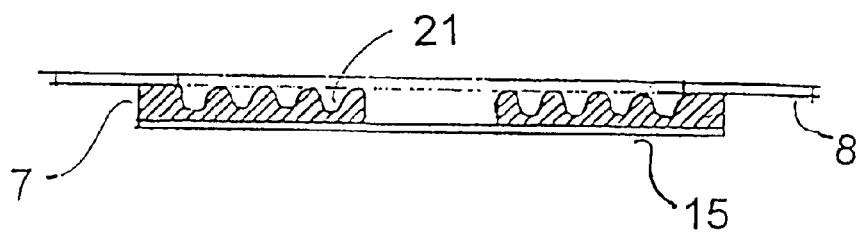
FIG. 8 shows a cross sectional view of yet a further embodiment of an ostomy appliance body side member according to the invention.

In the embodiment of FIG. 8 the sealing member is in the form of a uniform adhesive mass 7 provided with grooves 21 encircling the central hole. The sealing member is provided with a flange 8 and a release liner 15. This embodiment may also comprise a moldable backing covering the surface of the adhesive.

Figure 9:
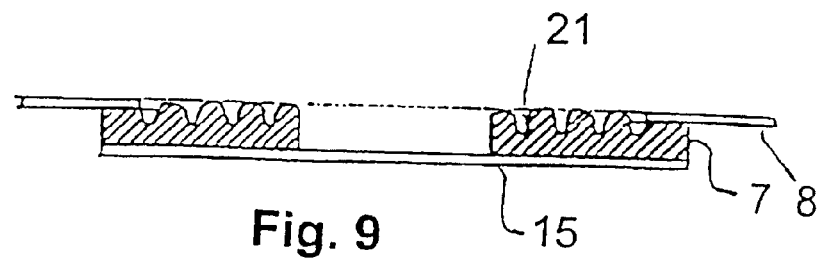
FIG. 9 shows a cross sectional view of the embodiment of FIG. 8 wherein the inner rim has been compressed.

In FIG. 9 the rim of the central hole has been enlarged by partially compressing the grooves 21 revealing a larger part of the surface of the release liner 15 below and of the indication of the size of the hole.

The sealing member of the invention may have any desired form, e.g., similar to the embodiments shown in W 098/17212.

In a first aspect, the invention relates to an ostomy appliance comprising a body side member comprising an adhesive wafer or pad for securing the appliance to the user's skin, the wafer or pad having a hole for receiving a stoma, and an optionally separately exchangeable receiving member or bag secured to the body side ostomy member for receiving secretions from the ostomy, which ostomy appliance is characterized by further comprising a separate or integrated sealing member disposed in the hole of the wafer or pad surrounding the stoma, the sealing member having a hole for accommodating the stoma and the sealing member having balanced plastic and elastic properties allowing an adaptation of the hole of the sealing member to a stoma by at least temporarily enlarging the hole by everting or rolling the inner rim of the hole for accommodating the stoma.

When the ostomy appliance of the invention has been placed over and around the stoma, the adhesive sealing member may recover essentially to the original form to fit snugly to the stoma. The "release" may be performed using, e.g., a finger or more or less automatically due to influence by elastic force, heat and/or humidity causing the sealing member to essentially resume its original shape.

In a preferred embodiment of the invention at least the area of a release liner covering the separate sealing member is provided with a guide for adaptation of the hole of an ostomy appliance to the size of an ostomy, the guide being visible from the side of the release liner facing the sealing member. In one embodiment, the guide is placed at the side of the release liner facing the sealing member. In another embodiment, the release liner is transparent and then the guide may be placed on either side.

An ostomy appliance according to this embodiment differs from known ostomy appliances comprising a guide for adaptation of the hole of an ostomy appliance to the size of an ostomy in that normally the guide is placed on the side of the release liner facing away from the sealing member and in that it is normally necessary to use scissors to cut according to the guide. Thus, according to the state of the art, it is necessary to use tools in order to adapt the size of the hole of an ostomy appliance to the size of an ostomy and, furthermore, the ostomy appliances of the state of the art do not offer a manner of secure sealing after adaptation by cutting. Both disadvantages of the appliances of the state of the art are overcome by the invention rendering the indication visible from the distal side of the body side member and rendering the adaptation of an ostomy appliance to the specific ostomy very simple using only the finger and independent of the use of tools. Furthermore it differs in that the balanced modulus against deformation and elasticity of the adhesive of a sealing member of an ostomy appliance of the invention is a result of the combined properties of a preferably substantially water-impervious backing layer or film and a skin friendly adhesive. Thus, in one extreme, the backing layer or film is elastic and the skin friendly adhesive is plastic and, in the opposite extreme, the backing layer or film is plastic and the skin friendly adhesive is elastic. Any combination of properties therebetween fulfilling the requirements will be suitable according to the invention.

In a second aspect, the invention relates to an ostomy appliance body side member comprising an adhesive waver or pad for securing the appliance to the user's skin, the wafer or pad having a hole for receiving a stoma, and a separate or integrated sealing member disposed in the hole of the wafer or pad surrounding the stoma wherein the sealing member disposed in the hole of the wafer or pad surrounding the stoma shows balanced plastic and elastic properties allowing an adaptation of the hole of the ostomy appliance to a stoma by enlarging the hole for accommodating the stoma, and wherein at least the area covering the separate sealing member is provided with a guide for adaptation of the hole of an ostomy appliance to the size of an ostomy, the guide being visible from the side of the release liner facing the sealing member. A body side member of the invention is preferably prepared so that a separately exchangeable receiving member or bag may be secured to the body side ostomy member for receiving secretions from the ostomy comprises a surface or coupling member for securing the separately exchangeable receiving member or bag.

In a third aspect, the invention relates to an ostomy sealing member in the form of a moldable mass or ring which shows a sufficient adhesiveness to secure the sealing member to the skin and seal around an ostomy and between the ostomy and an ostomy appliance adapted to receive secretions from the ostomy, which sealing member has a sufficient cohesion to be removed in one piece, independently of removal of the ostomy appliance without leaving remaining adhesive on the skin or the ostomy appliance, the sealing member having a hole for accommodating a stoma and the sealing member having balanced plastic and elastic properties allowing a temporary enlarging of the hole for receiving a stoma by everting or rolling the inner rim of the hole while placing the sealing member around the stoma.

In a fourth aspect, the invention relates to a method of applying an ostomy appliance body side member comprising an adhesive wafer or pad for securing the appliance to the user's skin, the wafer or pad having a hole comprising a sealing member having a hole for receiving a stoma wherein the hole of the sealing member is enlarged by everting the inner rim of the hole of the sealing member, adapting the hole to the size of the ostomy, aligning the stoma and the hole of the ostomy appliance body for accommodating the stoma and placing the body side member on the abdomen of the ostomate with the stoma projecting into the hole and bringing the sealing member to seal around the stoma, e.g., using a finger. The enlargement of the hole of the sealing member is preferably carried out by everting and rolling the inner ring forming a torus which after release will unroll and seal against the stoma without risk of formation of thin spots in the area around the stoma. The release may be effected manually using, e.g., a finger or by influence of humidity causing a hydrocolloid-containing adhesive to swell. Using a hydrocolloid-containing adhesive will further contribute to establishing a self-sealing effect around the stoma due to the swelling of the adhesive in use.

In the alternative, the sealing member may be provided with grooves encircling the central opening for an enlargement of the hole by lateral displacement outwardly of the rim compressing the grooves whereafter the sealing member will expand to provide a snug fit to the stoma.

Two different types of adhesives can be used for the sealing member—both being adaptable to the stoma without the use of tools and having the property that they may be everted or rolled or compressed for a sufficient span of time to apply an ostomy appliance.

1. Moldable adhesives which can be adapted to the stoma by displacement of the adhesive mass inwardly or outwardly whereby it forms a protective mass surrounding the stoma.

2. Flexible adhesives which can be adapted to the stoma due to the flexibility and compliance whereby it forms a protective layer on the peristomal skin surrounding the stoma.

The moldable adhesive used in the different compositions of the sealing member is preferably characterized as being a hypoallergenic putty-like adhesive. The adhesive may preferably comprise some memory allowing for a displacement of adhesive to adapt an ostomy appliance to a stoma by enlarging the hole for accommodating the stoma, whereafter the adhesive recovers essentially to the original form. The memory or elasticity must not, however, be so pronounced that a constriction of the stoma occurs.

The skin-friendly adhesive may be a skin-friendly adhesive known per se, e.g., an adhesive comprising hydrocolloids or other moisture absorbing constituents for prolonging the time of use. The adhesive may suitably be of the type disclosed in GB Patent Specification No. 1 280 631, in DK Patent Specifications Nos. 127,578, 148,408, 154,806, 147, 226 and 154,747, in EP published application Nos. 0 097 846 and 0 415 183, in SE Published Application No. 365,410, in WO Publication No. 88/06894, in U.S. Patent Specification No. 4,867,748, and in NO published application No. 157,686. Especially preferred are the adhesives disclosed in U.S. Pat. Nos. 4,367,732 and 5,051,259 and DK Patent Specification No. 169,711.

A medical grade adhesive may be used for securing the sealing member to the peristomal skin. A variety of such barrier adhesives are known in the art and may be used here, one such formulation being disclosed, for example, in DK Patent Specification 147035 and U.S. Pat. No. 4,551,490. The moldable adhesive may be composed of a hypoallergenic, soft, easily-deformable, non-memory putty-like adhesive material and is preferably a hydrocolloid based adhesive or a hydrogel. The moldable backing, e.g., Parafilm® or a polymer solution which is sprayed on the surface, protects the surface of the moldable mass against dissolution by secretions from the stoma and prevents a tacky surface on the side facing the bag.

The backing layer or film may be of any suitable material known per se for use in the preparation of ostomy appliances or wound dressings, e.g., a foam, a non-woven layer or a film of polyurethane, polyethylene, polyester or polyamide or optionally a copolymer thereof. In accordance with the invention it has surprisingly been found that by use of a thinner backing layer or film than is normally used when preparing ostomy appliances, an improved adaptability is obtained at the same time as the modulus is reduced. The modulus may be from 1 to 10 N/mm$^2$, preferably from 2 to 5 N/mm$^2$. These properties may be obtained using the same load of adhesive as is conventionally used, and thus, the conventional properties of the adhesive are retained as opposed to the case in which the load of adhesive was lowered generally giving a risk of insufficient tack and adhesive properties. The layer of adhesive may preferably be thinner along the inner rim of the adhesive sealing member to improve the moldability.

Using a layer or film having a low modulus allowing an easy deformation during application but yet a sufficiently high elasticity to essentially prevent deformation after application ensures that the adhesive does not constrict the stoma when recovering to establish a snug sealing against the stoma.

The medical grade adhesive secures the unit to the peristomal skin. The flexible backing protects the surface of the adhesive against dissolution by secretions from the stoma and prevents a tacky surface on the side facing the bag.

This embodiment offers the following advantages: it is simple/easy to handle, it may be adapted to a stoma without use of tools, it gives rise to no or very little residues on skin after removal, it gives rise to no or little erosion of adhesive, it may easily be adapted to complicated shapes of the stoma and it reduces the risk of an insufficient sealing when disposing or extruding moldable sealing material towards the stoma.

The adhesive is preferably a pressure sensitive adhesive having a high degree of plasticity. The ratio between plastic (viscous) modulus and elastic modulus is often referred to as the tangens delta value. A tangens delta value between 0.5 and 1.2, preferably between 0.8 and 1.0, has been shown to be suitable combined with an elastic modulus (G') of at least $10^2$ Pa, preferably of at least $10^4$ Pa. The tangens delta value of conventional PSAs is normally from 0.4 to 0.8.

Adhesives of a non-memory type may, e.g., be a homogeneous mixture of a pressure sensitive adhesive component, mineral oil, and hydrocolloid gums or cohesive strengthening agents as the mass disclosed in U.S. Pat. No. 4,204,540. The mass may also be a composition including one or more hydrocolloids, a film former which is butyl ester of polycarboxylic resin formed from vinyl methyl ether and maleic anhydride, a plasticizer, a thickening agent and an alcohol solvent as disclosed in EP Patent No. 0 048 556. A further paste is disclosed in U.S. Pat. No. 5,369,130. This composition comprises a liquid rubber component and a filler component. The rubber component is a diene-type liquid rubber, preferably butadiene- or isoprene-type. The filler component is selected from the groups consisting of inorganic fillers, natural polymers, semisynthetic water-soluble polymers and synthetic water-soluble polymers. A further composition of a skin protective gel containing polyvinyl methylether or monoisopropyl ester of polyvinylmethylether maleic acid is disclosed in U.S. Pat. No. 3,876,771. The composition is made up of a film forming protective colloidal material in combination with a solvent and a gelling agent. Isopropanol is the solvent, monoisopropyl ester of polyvinyl methylether/maleic acid is a film former and polyvinylpyrrolidone, polyvinyl methylether, polyacrylic acid and hydroxypropyl cellulose are the gelling agents. A hydrophilic elastomeric pressure sensitive material is disclosed in U.S. Pat. No. 4,750,482. This composition is a water-insoluble, hydrophilic, pressure-sensitive adhesive including at least one irradiation cross-linked synthetic organic polymer (predominantly derived from vinylpyrrolidone) and an adhesive plasticizer (polyethylene glycol).

The composition disclosed in EP 0 048 556 B1 suffers from the drawback that it comprises a considerable amount (25% to 45% by weight) of alcohol, ethanol and isopropanol being preferred. When using such a paste, it is observed that there is only a limited time for forming the paste after the application as the paste cures when exposed to air. Furthermore, the amount of alcohol trapped in the paste must be minimized in order to avoid less attractive physical properties due to an adverse effect on the properties of the adhesive of an ostomy appliance which is placed upon the paste. Still further, the considerable amount of alcohol may irritate the skin and such a composition is not advisable to use on skin which has been sensitized.

The pastes disclosed in U.S. Pat. No. 4,204,540 suffer from the drawback that the shapeability is very dependent on the content of mineral oil. If an insufficient amount of mineral oil is added the composition will be too tough to shape and if too much mineral oil is added the composition becomes sticky and difficult to handle. Generally, pastes consisting of polyisobutylene, butyl rubber and mineral oil may be very hard, if the content of butyl rubber is high and hence, the paste will be difficult to shape, or it will be very soft and liquid if the content of butyl rubber is low and the content of mineral oil is high.

A preferred adhesive composition to be used in the ostomy appliances of the invention is an adhesive composition comprising a water-dispersible polyester having a very rapid water absorption and improved wet tack and, at the same time, resistance to disintegration upon contact with body fluids.

A preferred non-memory putty-like mass to be used according to the invention is in the form of a moldable mass of a hypo-allergenic, substantially non-memory putty-like adhesive comprising a) a blockcopolymer having a major content of di-block copolymer, b) a tackifying liquid constituent, and c) a waxy constituent.

In a preferred embodiment the sealing member has a flange stretching from the outer rim thereof. Such a flange preferably has adhesive on the surface and provides extra security against leaks and prevents direct contact between the exudates and the coupling part of the ostomy device. Thus, pollution or contamination of parts of the body side member during service or exchange of receiving member or bag is avoided. Avoidance of pollution or contamination of the body side member is of great importance when extending the weartime of the body side member as remains of the exudate on the body side member which may cause odor are avoided.

Additionally, this embodiment renders it possible to separate the two functions of the sealing around an ostomy and the securing of a separately exchangeable receiving member or bag for receiving secretions from an ostomy to a body side ostomy member in that it is not mandatory that the securing of the separately exchangeable receiving member to the body side ostomy member is impervious to liquid.

The separately exchangeable receiving member or bag may be secured to the body side ostomy member using an adhesive adhering to a flange or by mechanical means. Mechanical fastening means for securing the separately exchangeable receiving member or bag releasably to the body side ostomy member may, e.g., be a traditional coupling system using a coupling ring or a zip-like fastener, snaps, buckles, buttons or rings.

A zip-like fastener may, e.g., be of the type known for closing plastic bags, e.g., marketed under the trademark Minigrip®.

A fastening means may also be placed between the separate sealing member disposed in the hole of the wafer or pad surrounding the stoma and the body side member.

In a preferred embodiment of the invention, the attachment is placed between the sealing member disposed in the hole of the wafer or pad surrounding the stoma and the body side member using an adhesive. This embodiment renders it simple to discriminate between the securing of the separately exchangeable receiving member or bag for receiving secretions from an ostomy and of the separate sealing member disposed in the hole of the wafer or pad surrounding the stoma. Thus, it is simple to decide whether to exchange only the receiving member or bag or to exchange the receiving member or bag and the separate sealing member disposed in the hole of the wafer or pad surrounding the stoma.

Materials and Methods

Kraton® G1726 from Shell: Styrene-ethylenebutylene-styrene copolymer (SEBS) having a molecular weight of 45,000 as determined by GPC and a content of diblock copolymer of 70%.

Kraton® D1118 from Shell: Styrene-butadiene-styrene copolymer (SBS) having a molecular weight of 103,000 (GPC) and a content of diblock copolymer of 80%.

Vector® 4114 from Exxon: Styrene-isoprene-styrene copolymer (SIS) having a molecular weight of 130,000 and a content of diblock copolymer of 40% and 15% styrene.

Vistanex® LM-MH from Exxon: Polyisobutylene (PIB) having a molecular weight of 90,000 (GPC).

AQ1045 from Eastman: A branched water-dispersible polyester having a Brookfield viscosity at 177° C. of 3,000–6,000 cP.

AQ1350 from Eastman: A branched water-dispersible polyester having a Brookfield viscosity at 177° C. of 28,000–45,000 cP.

Kraton® D1107 from Shell Chemical Company: Styrene-isoprene-styrene copolymer (SIS) having a molecular weight of 212,000–260,000 as determined by GPC and 15% styrene.

LVSI101 from Shell Chemical Company: Styrene-isoprene diblock copolymer (SI) having a molecular weight of about 30,000 as determined by GPC and 13% styrene.

Wax Total 40/60 from TOTAL.

Petroleum jelly: Vaselinum Album from Witco.

Dioctyladipate from International Speciality Chemicals Ltd.: A plasticizer.

METALYN 200: A methyl ester of rosin from Hercules.

Eastoflex E1003, E1060 and E1200 from Eastman: Propylene-ethylene copolymers.

Eastoflex D127 from Eastman: A propylene/1-hexene copolymer.

Vestoplast 704, 708 and 750: Amorphous propylene-rich poly-α-olefins from Hüls Chemie.

Wingtack 10 from Goodyear: A liquid polyterpene tackifier resin.

Arkon P-90 from Arakawa Forest Chemical Industries Ltd.: A hydrogenated cyclopentadiene resin.

Polybutene oil: Hyvis® 10 from BP having a molecular weight of 1,500.

Polybutene: Hyvis® 2000 from BP having a molecular weight Mw of 30,000.

Mineral Oil: PL 500 from Parafluid Mineral Oel.

Tackifier resin: Regalite® R91 resin from Hercules or Arkon® P-90 resin from Arakawa. Glycerol.

PEG 400 from Hoechst: Polyethylene glycol.

Sodium carboxymethylcellulose: Akucell® AF2881 from Akzo or Blanose® 9H4XF from Hercules Corp.

Guar gum: Guar Gum FG 200 from Nordisk Gelatine.

Pectin:Pektin LM 12CG Z from Copenhagen Pectin or Pektin USP/100 from Copenhagen Pectin.

Klucel HXF EP: Hydroxypropyl cellulose.

Gelatin: Gelatine P.S.98.240.233 from ED. Geistlich Sohne AG.

Zinc Oxide: Zinkoxid Pharma from Hoechst AG.

A Z mixer Type LKB 025 from Herman-Linden was used.

Experimental Part

EXAMPLE 1.

Preparation of a moldable mass to be used according to the invention.

100 grams of Kraton® G1726 was used and the amounts of other ingredients used correspond to the composition stated in Table 1.

Equal amounts of Kraton® G1726 (SEBS) and of Vistanex® LM-MH were mixed in a Z Mixer for 20 minutes at 160° C. under a vacuum of 100 mbar. Then, the vacuum was released, the mixing was continued at 160° C. for 10 minutes and the remains of Vistanex® LM-MH, the wax, and petroleum jelly were admixed and mixed for 10 minutes each. Then, the heating was turned off, and guar gum was added at maximum 90° C. under a vacuum of 100 mbar and mixed for 10 minutes. Finally, pectin, gelatine and zinc oxide were admixed at a temperature of 90° C. and mixed for 10 minutes.

EXAMPLE 2

Preparation of a Moldable Mass to be Used According to the Invention. 100 grams of Kraton® G1726 was used and the amounts of other ingredients used correspond to the composition stated in Table 1.

Equal amounts of Kraton® G1726 (SEBS) and Vistanex® LM-MH were mixed in a Z Mixer for 20 minutes at 160° C. under a vacuum of 100 mbar. Then, the vacuum was released, the mixing was continued at 160° C. for 10 minutes and the remains of Vistanex® LM-MH, the wax, and Hyvis® 10 or PL 500 were admixed and mixed for 10 minutes each. Then, the heating was turned off, and guar gum was added at maximum 90° C. under a vacuum of 100 mbar and mixed for 10 minutes. Finally, pectin, gelatine and zinc oxide were admixed at a temperature of 90° C. and mixed for 10 minutes.

EXAMPLES 3–5

Preparation of Moldable Masses to be Used According to the Invention.

In the same manner as described in Example 2 above, moldable masses according to the invention were produced having the compositions stated below in Table 1.

TABLE 1

Composition of moldable masses of the invention of Examples 1–5 stated in % by weight

| Component | Example 1 | Example 2 | Example 3 | Example 4 | Example 5 |
| --- | --- | --- | --- | --- | --- |
| SEBS | 5 | 5 | 5 | 10 | 8 |
| PIB | 30 | 15 | 15 | 10 | 18 |
| Microcrystalline wax | 5 | 5 | 5 | 5 | 5 |
| Petroleum jelly | 10 | | | | |
| Polybutene oil | | 25 | | | |
| Liquid paraffin | | | 25 | 25 | 20 |
| CMC | | | 12 | 20 | 15 |
| Guar Gum | 15 | 20 | | | |
| Pectin | 15 | 10 | 10 | 10 | 8 |
| Gelatine | 18 | 17.5 | 27 | 20 | 25 |
| Zinc white | 2 | 2.5 | 1 | | 3 |

EXAMPLE 6.

Preparation of a Moldable Mass to be Used According to the Invention.

Equal amounts of Kraton® G1726 (SEBS) and Hyvis® 2000 were mixed in a Z Mixer for 30 minutes at 160° C. under a vacuum of 100 mbar and the Hyvis®) 2000 was added in four parts to ensure homogeneity during the admixing over a period of 20 minutes. Then, the remains of Hyvis® 2000 was added in four parts at 160° C. over 30 minutes and the vacuum was released. The Hyvis® D10 was added in four parts and mixed for 15 minutes. Wax was added and mixed for 10 minutes. Then, the heating was turned off, and guar gum and CMC were added at maximum 90° C. under a vacuum of 100 mbar and mixed for 10 minutes. Finally, pectin, gelatine and zinc oxide were admixed at a temperature of 90° C. and mixed for 10 minutes.

EXAMPLES 7–8
Preparation of Moldable Masses to be Used According to the Invention.

In the same manner as described in the Example 2 above, moldable masses according to the invention were produced having the compositions stated below in Table 2.

TABLE 2

Composition of moldable masses of the invention of Example 6–8 stated in % by weight.

| Component | Example 6 | Example 7 | Example 8 |
|---|---|---|---|
| SEBS (Diblock content about 70%) | 5 | | |
| SIS (Diblock content about 40%) | | 5 | |
| SB (Diblock content about 80%) | | | 5 |
| PIB | | 15 | 15 |
| Polybutene ($M_w$ 30,000) | 15 | | |
| Polybutene oil | 25 | 25 | 25 |
| Microcrystalline wax | 5 | 5 | 5 |
| CMC | 10 | 13 | 25 |
| Guar Gum | 15 | | |
| Pectin | 5 | 10 | 8 |
| Gelatine | 18 | 22 | 15 |
| Zinc white | 2 | 5 | 2 |

EXAMPLES 9–10
Preparation of Moldable Masses to be Used According to the Invention.

Equal amounts of Kraton® G1726 (SEBS) and Hyvis® 2000 were mixed in a Z Mixer for 30 minutes at 160° C. under a vacuum of 100 mbar and the Hyvis® 2000 was added in four parts to ensure homogeneity during the admixing over a period of 20 minutes.

Then, the remains of Hyvis® 2000 was added in four parts at 160° C. over 30 minutes and the vacuum was released. The Hyvis® 10 was added in four parts and mixed for 15 minutes. Resin and wax was added and mixed for 10 minutes each. Then, the heating was turned off, and CMC were added at maximum 90° C. under a vacuum of 100 mbar and mixed for 10 minutes. Finally, pectin, gelatine and zinc oxide were admixed at a temperature of 90° C. and mixed for 10 minutes.

TABLE 3

Composition of moldable masses of the invention of Examples 9–10 stated in % by weight:

| Component | Example 9 | Example 10 |
|---|---|---|
| SEBS (Diblock content about 70%) | 5 | 5 |
| Polybutene ($M_w$ 30,000) | 10 | 5 |
| Polybutene oil | 25 | 25 |
| Resin | 5 | 10 |
| Microcrystalline wax | 5 | 5 |
| CMC | 15 | 15 |
| Pectin | 10 | 10 |
| Gelatine | 24 | 24 |
| Zinc white | 1 | 1 |

The pastes produced in the above Examples are ready to use but may preferably be packed in metered amounts, e.g., in a blister pack or rod for shipment. A rod may be rolled and have a release liner on one or both sides. The produce is preferably produced and packed under aseptic conditions.

Preparation o preferred adhesives to be used according to the invention is disclosed in the following Examples.

Example 11

An adhesive agent having the composition stated in Table 4 was prepared in a Z-blade mixer. Before the mixing, the mixing chamber was heated to 140° C. by means of an oil heater. AQ1045, Eastoflex D127, Eastoflex E1003, dioctyladipate and the hydrocolloids were weighed out separately. Firstly Eastoflex D127 and E1003 were mixed for 15 minutes. AQ1045 was added and the mixing continued for 10 minutes. Dioctyladipate was added and mixed for additional 10 minutes. The heat supply was turned off and the mixing chamber was cooled to 80° C. The hydrocolloids (a mixture of pectin, hydroxypropyl cellulose and gelatine in the ratio 1:1.5:1) were added and the mixing was continued in vacuum for a total mixing time of 60 minutes. The adhesive agent was removed from the mixer and pressed into 1 mm thin plates between two sheets of silicon paper in a hydraulic press at 90° C.

Example 12

An adhesive agent having the composition stated in Table 4 was prepared in a Z-blade mixer. Before the mixing, the mixing chamber was heated to 140° C. by means of an oil heater. AQ1350, Eastoflex D127, Eastoflex E1003, Wingtack 10 and dioctyladipate were weighed out separately. Firstly Eastoflex D127 and E1003 were mixed for 15 minutes. AQ1350 was added and the mixing continued for 10 minutes. Wingtack 10 was added and mixed for an additional 10 minutes and finally dioctyladipate was added. The adhesive agent was removed from the mixer and pressed into 1 mm thin plates between two sheets of silicon paper in a hydraulic press at 90° C.

Example 13

An adhesive agent having the composition stated in Table 4 was prepared in a Z-blade mixer. Before the mixing, the mixing chamber was heated to 150° C. by means of an oil heater. AQ1045, Vector 4114, LVSI101, dioctyladipate and the hydrocolloids were weighed out separately. Firstly Vector and dioctyladipate were mixed at 150° C. for 15 minutes. LVSI101 was added and the mixing continued for 10 minutes. The mixing chamber was cooled to 130° C. and AQ1045 was added and the mixing was continued for an additional 15 minutes. The heat supply was turned off and the mixing chamber was cooled to 80° C. The hydrocolloids, a mixture of pectin and hydroxypropylcellulose in the ratio 1:1, and finally zinc oxide were added and the mixing was continued in vacuum for a total mixing time of 60 minutes. The adhesive agent was removed from the mixer and pressed into 1 mm thin plates between two sheets of silicon paper in a hydraulic press at 90° C.

Example 14

An adhesive agent having the composition stated in Table 4 was prepared in a Z-blade mixer. Before the mixing, the mixing chamber was heated to 130° C. by means of an oil heater. AQ1045 and glycerol and the hydrocolloids were weighed out separately. Firstly AQ1045 and glycerol were mixed at 130° C. for 15 minutes. The heat supply was turned off and the mixing chamber was cooled to 80° C. The hydrocolloids, a mixture of pectin and gelatine in the ratio 1:2, were added and the mixing continued in vacuum for a mixing time of 40 minutes. The adhesive agent was removed from the mixer and is pressed into 1 mm thin plates between two sheets of silicon paper in a hydraulic press at 90° C.

Example 15

An adhesive agent having the composition stated in Table 4 was prepared in a Z-blade mixer. Before the mixing, the mixing chamber was heated to 130° C. by means of an oil heater. AQ1045 and PEG400 and the hydrocolloids were weighed out separately. Firstly AQ1045 and PEG400 were mixed at 130° C. for 15 minutes. The heat supply was turned off and the mixing chamber was cooled to 80° C. The hydrocolloids, a mixture of hydroxypropylcellulose and gelatine in the ratio 1:1, were added and the mixing continued in vacuum for a total mixing time of 40 minutes. The adhesive agent was removed from the mixer and pressed into 1 mm thin plates between two sheets of silicon paper in a hydraulic press at 90° C.

Example 16

An adhesive agent having the composition stated in Table 4 was prepared in a Z-blade mixer. Before the mixing, the mixing chamber was heated to 150° C. by means of an oil heater. AQ1045, Vector 4114, LVSI101, Arkon P-90 and the hydrocolloids were weighed out separately. Firstly Vector was mixed at 150° C. for 15 minutes. LVSI101 was added and the mixing continued for 15 minutes. The mixing chamber was cooled to 130° C. and Arkon P-90 followed by AQ1045 were added and the mixing was continued for an additional 30 minutes. The heat supply was turned off and the mixing chamber was cooled to 80° C. The pectin was added and the mixing was continued in vacuum for a total mixing time of 90 minutes. The adhesive agent was removed from the mixer and pressed into 1 mm thin plates between two sheets of silicon paper in a hydraulic press at 90° C.

TABLE 4

| Constituent | Example 11 | Example 12 | Example 13 | Example 14 | Example 15 | Example 16 |
|---|---|---|---|---|---|---|
| AQ 1045 | 35 | | 30 | 50 | 40 | 30 |
| AQ 1350 | | 50 | | | | |
| LVSI 101 | | | 29 | | | 25 |
| Vector 4114 | | | 5 | | | 5 |
| Dioctyladipate | 5 | 5 | 5 | | | |
| Eastoflex D127 | 15 | 15 | | | | |
| Eastoflex E1003 | 10 | 15 | | | | |
| Wingtack 10 | | 15 | | | | |
| Arkon P-90 | | | | | | 10 |
| Glycerol | | | | 20 | | |
| PEG 400 | | | | | 20 | |
| Blanose 9H4XF | | | | | | |
| Pectin USP/100 | 10 | | 15 | 10 | | 30 |
| Klucel HXF EP | 15 | | 15 | | 20 | |
| Gelatine | 10 | | | 20 | 20 | |
| Zinc oxide | | | | 1 | | |

EXAMPLES 17–21

Adhesives being suitable as pastes having the compositions stated in Table 5 were prepared in a Z-mixer in the same manner as described in Example 11.

TABLE 5

| Constituent | Example 17 | Example 18 | Example 19 | Example 20 | Example 21 |
|---|---|---|---|---|---|
| Eastoflex E 1003 | 15 | 15 | 15 | 20 | 20 |
| Eastoflex E 1060 | | | | 2.5 | 2.5 |
| AQ 1350 | 35 | 35 | 35 | 35 | 35 |
| Dioctyladipate | 5 | | 5 | 5 | |
| Metalyn 200 | | 5 | | | 5 |
| Vestoplast 708 | 10 | | 5 | 2.5 | 2.5 |
| Vestoplast 704 | | 5 | 2.5 | | |
| Vestoplast 750 | 10 | | 2.5 | | |
| Gelatine | 10 | 10 | 10 | 10 | 10 |
| Pectin | 15 | 10 | 10 | 10 | 10 |
| Klucel | | 15 | 15 | 15 | 15 |

What is claimed is:

1. An ostomy appliance comprising a body side member (1) comprising an adhesive wafer or pad (2) for securing the appliance to a user's skin, said wafer or pad having a first hole for receiving a stoma, and optionally a separately exchangeable receiving member or bag (4) secured to the body side member for receiving secretions from the ostomy, the ostomy appliance further comprising a sealing member (5) disposed in the first hole of the wafer or pad surrounding the stoma, said sealing member having a second hole (3) for accommodating the stoma and said sealing member having balanced plastic and elastic properties allowing an adaptation of the second hole to the stoma by a temporary enlarging of the second hole by everting or rolling an inner rim of the second hole for accommodating the stoma.

2. An ostomy appliance as claimed in claim 1, further comprising a release line (15) covering at least the sealing member (5) provided with a guide for adaptation of the second hole of the ostomy appliance to the size of the ostomy, said guide being visible from the side of the release liner facing the sealing member.

3. As ostomy appliance as claimed in claim 1, wherein the sealing member (5) is in the form of a moldable mass or ring (7) of a hypoallergenic, adhesive having a backing layer or film (14).

4. An ostomy appliance as claimed in claim 1, wherein the sealing member (5) has a flange (8,16) extending from an outer rim thereof.

5. An ostomy appliance as claimed in claim 1, wherein the separately exchangeable receiving member or bag (4) is releasably secured to the body side member (1) by an adhesive or by mechanical fastening means.

6. An ostomy appliance as claimed in claim 5, wherein the mechanical fastening means is a coupling ring, a zip-like fastener, snaps, buckles, buttons, or rings.

7. An ostomy appliance body side member (1) comprising an adhesive wafer or pad (2) for securing the appliance to a user's skin, said wafer or pad having a first hole for receiving a stoma, and optionally an exchangeable sealing member (5) disposed in the first hole of the wafer or pad surrounding the stoma wherein the sealing member disposed in the first hole of the wafer or pad surrounding the stoma has balanced plastic and elastic properties allowing an adaptation of a hole of the ostomy appliance to the stoma by a temporary enlarging of the second hole by everting or rolling an inner rim of the second hole for accommodating the stoma.

8. An ostomy appliance body side member (1) as claimed in claim 7, further comprising a surface or coupling member (11,18) for securing a separately exchangeable receiving member or bag (4) to the body side member for receiving secretions from the ostomy.

9. An ostomy sealing member (5) in the form of a moldable mass or ring which has a sufficient adhesiveness to secure a sealing member to skin and seal around an ostomy and between the ostomy and an ostomy appliance adapted to receive secretions from the ostomy, which sealing member has a sufficient cohesion to be removed in one piece, independently of removal of the ostomy appliance, without leaving adhesive remaining on the skin or the ostomy appliance, said sealing member having a hole (3) for accommodating a stoma and said sealing member having balanced plastic and elastic properties allowing a temporary enlarging of the hole for receiving the stoma by everting or rolling an inner rim of the hole while placing the sealing member around the stoma.

10. A method of applying an ostomy appliance body side member (1) comprising an adhesive wafer or pad (2) for securing the appliance to a user's skin, said wafer or pad having a first hole comprising a sealing member (5) having a second hole for receiving a stoma wherein the second hole of the sealing member is enlarged by everting or rolling an inner rim of the second hole of the sealing member adapting the second hole to the size of the ostomy, aligning the stoma and the second hole of the ostomy appliance body for accommodating the stoma and placing the body side member on the abdomen of the ostomate with the stoma projecting into the second hole and bringing the sealing member to seal around the stoma.

* * * * *